(12) United States Patent
Hashimoto et al.

(10) Patent No.: US 8,865,896 B2
(45) Date of Patent: Oct. 21, 2014

(54) METHOD FOR PREPARING ADENINE COMPOUND

(75) Inventors: Kazuki Hashimoto, Osaka (JP); Wataru Katoda, Osaka (JP); Kazuhiko Takahashi, Osaka (JP); Ayumu Kurimoto, Osaka (JP)

(73) Assignees: Astrazeneca Aktiebolag, Sodertalje (SE); Dainippon Sumitomo Pharma Co., Ltd., Osaka (JP)

( * ) Notice: Subject to any disclaimer, the term of this patent is extended or adjusted under 35 U.S.C. 154(b) by 474 days.

(21) Appl. No.: 12/863,291

(22) PCT Filed: Jan. 16, 2009

(86) PCT No.: PCT/JP2009/050550
§ 371 (c)(1),
(2), (4) Date: Jul. 16, 2010

(87) PCT Pub. No.: WO2009/091032
PCT Pub. Date: Jul. 23, 2009

(65) Prior Publication Data
US 2011/0046369 A1    Feb. 24, 2011

(30) Foreign Application Priority Data

Jan. 17, 2008    (JP) .................................. 2008-007974

(51) Int. Cl.
C07D 473/02    (2006.01)
C07D 413/14    (2006.01)
C07D 473/18    (2006.01)

(52) U.S. Cl.
CPC ................... C07D 473/18 (2013.01)
USPC .......................... 544/276; 544/118

(58) Field of Classification Search
CPC .................................................... C07D 473/18
USPC ................................................ 544/118, 276
See application file for complete search history.

(56) References Cited

U.S. PATENT DOCUMENTS

| | | | |
|---|---|---|---|
| 5,736,549 | A | 4/1998 | Beasley et al. |
| 5,994,361 | A | 11/1999 | Penney et al. |
| 6,028,076 | A | 2/2000 | Hirota et al. |
| 6,110,923 | A | 8/2000 | Ely |
| 6,329,381 | B1 | 12/2001 | Kurimoto et al. |
| 6,376,501 | B1 | 4/2002 | Isobe et al. |
| 6,448,236 | B1 | 9/2002 | Monaghan |
| 6,630,478 | B2 | 10/2003 | Diamond et al. |
| 6,887,880 | B2 | 5/2005 | Levy et al. |
| 7,157,465 | B2 | 1/2007 | Isobe et al. |
| 7,521,454 | B2 | 4/2009 | Isobe et al. |
| 7,642,350 | B2 | 1/2010 | Pryde |
| 7,691,877 | B2 | 4/2010 | Jones et al. |

(Continued)

FOREIGN PATENT DOCUMENTS

| CA | 1220148 | 4/1987 |
|---|---|---|
| EP | 1 220 862 | 7/2002 |

(Continued)

OTHER PUBLICATIONS

Presentation by Tom McInally at RSC BMSC Inflammation meeting entitled "Identification and Pharmacology of Novel TLR7 Agonist Antedrugs" (Nov. 18, 2010).*

(Continued)

*Primary Examiner* — Andrew D Kosar
*Assistant Examiner* — John S Kenyon
(74) *Attorney, Agent, or Firm* — Finnegan, Henderson, Farabow, Garrett & Dunner LLP

(57) ABSTRACT

A method for producing adenine compound (1):

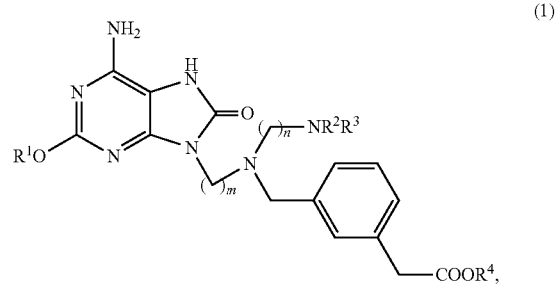

wherein m and n are independently an integer of 2 to 5, $R^1$ is $C_{1-6}$ alkyl group, $R^2$ and $R^3$ are the same or different, and hydrogen atom, or $C_{1-6}$ alkyl group, or $R^2$ and $R^3$ are combined with an adjacent nitrogen atom to form pyrrolidine, morpholine, piperidine, piperazine, etc., and $R^4$ is $C_{1-3}$ alkyl group, which comprises a step of reacting compound (2):

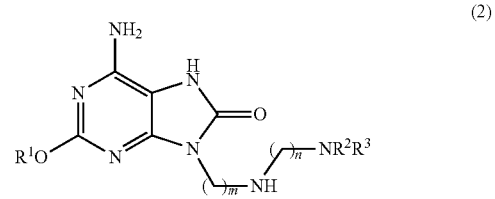

and compound (3):

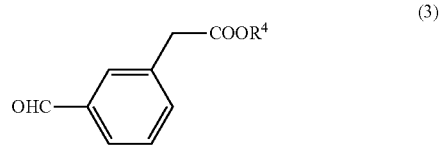

in the presence of a boron-containing reducing agent.

18 Claims, 1 Drawing Sheet

(56) References Cited

U.S. PATENT DOCUMENTS

| | | | |
|---|---|---|---|
| 2002/0040032 A1 | 4/2002 | Glasky et al. | |
| 2002/0061899 A1 | 5/2002 | Diamond et al. | |
| 2002/0068745 A1 | 6/2002 | Levy et al. | |
| 2002/0128264 A1 | 9/2002 | Taylor | |
| 2003/0187261 A1* | 10/2003 | Havlicek et al. | 544/276 |
| 2003/0191086 A1 | 10/2003 | Hanus et al. | |
| 2004/0132748 A1 | 7/2004 | Isobe et al. | |
| 2006/0052403 A1 | 3/2006 | Isobe et al. | |
| 2006/0252774 A1 | 11/2006 | Vatner | |
| 2006/0264448 A1 | 11/2006 | Pryde | |
| 2007/0190071 A1 | 8/2007 | Kurimoto et al. | |
| 2007/0197478 A1 | 8/2007 | Jones et al. | |
| 2007/0225303 A1 | 9/2007 | Ogita et al. | |
| 2007/0249638 A1 | 10/2007 | Giorgio et al. | |
| 2008/0008682 A1 | 1/2008 | Chong et al. | |
| 2008/0269240 A1 | 10/2008 | Hashimoto et al. | |
| 2008/0300244 A1 | 12/2008 | Bonnert et al. | |
| 2009/0047249 A1 | 2/2009 | Graupe et al. | |
| 2009/0082332 A1 | 3/2009 | Abbot et al. | |
| 2009/0099216 A1 | 4/2009 | Millichip et al. | |
| 2009/0105212 A1 | 4/2009 | Isobe et al. | |
| 2009/0118263 A1 | 5/2009 | Hashimoto et al. | |
| 2009/0131458 A1 | 5/2009 | Lazarides et al. | |
| 2009/0143400 A1 | 6/2009 | McInally et al. | |
| 2009/0192153 A1 | 7/2009 | Hashimoto et al. | |
| 2009/0202484 A1 | 8/2009 | Chong et al. | |
| 2009/0281075 A1 | 11/2009 | Roughton et al. | |
| 2009/0324551 A1 | 12/2009 | Carson et al. | |
| 2009/0325877 A1 | 12/2009 | Grunt et al. | |
| 2010/0075995 A1 | 3/2010 | Biggadike et al. | |
| 2010/0087443 A1 | 4/2010 | Bonnert et al. | |
| 2010/0093998 A1 | 4/2010 | Isobe et al. | |
| 2010/0099870 A1 | 4/2010 | Isobe et al. | |
| 2010/0120799 A1 | 5/2010 | Lazarides et al. | |
| 2010/0130491 A1 | 5/2010 | Bonnert et al. | |
| 2010/0240623 A1 | 9/2010 | Cook et al. | |
| 2010/0280001 A1 | 11/2010 | Bonnert et al. | |
| 2011/0054168 A1* | 3/2011 | Kurimoto et al. | 544/118 |
| 2011/0294802 A1* | 12/2011 | Mcinally et al. | 514/234.2 |

FOREIGN PATENT DOCUMENTS

| | | |
|---|---|---|
| JP | 10-501533 | 2/1998 |
| JP | 10-507171 | 7/1998 |
| JP | 11-180981 | 7/1999 |
| JP | 11-180982 | 7/1999 |
| JP | 11-193282 | 7/1999 |
| JP | 2000-159767 | 6/2000 |
| JP | 2003-511460 | 3/2003 |
| JP | 2005-089334 | 4/2005 |
| WO | WO 95/35297 | 12/1995 |
| WO | WO 96/11200 | 4/1996 |
| WO | WO 00/43394 | 7/2000 |
| WO | WO 01/27131 | 4/2001 |
| WO | WO 02/04449 | 1/2002 |
| WO | WO 02/04451 | 1/2002 |
| WO | WO 02/40481 | 5/2002 |
| WO | WO 03/011864 | 2/2003 |
| WO | WO 2005/092892 | 10/2005 |
| WO | WO 2005/092893 | 10/2005 |
| WO | WO 2006/117670 | 11/2006 |
| WO | WO 2007/024707 | 3/2007 |
| WO | WO 2007/031726 | 3/2007 |
| WO | WO 2007/034173 | 3/2007 |
| WO | WO 2007/034817 | 3/2007 |
| WO | WO 2007/034881 | 3/2007 |
| WO | WO 2007/034882 | 3/2007 |
| WO | WO 2007/034916 | 3/2007 |
| WO | WO 2007/034917 | 3/2007 |
| WO | WO 2007/093901 | 8/2007 |
| WO | WO 2008/004948 | 1/2008 |
| WO | WO 2008/005555 | 1/2008 |
| WO | WO 2008/071976 | 6/2008 |
| WO | WO 2008/101867 | 8/2008 |
| WO | WO 2008/114006 | 9/2008 |
| WO | WO 2008/114008 | 9/2008 |
| WO | WO 2008/114817 | 9/2008 |
| WO | WO 2008/114819 | 9/2008 |
| WO | WO 2008/135791 | 11/2008 |
| WO | WO 2009/005687 | 1/2009 |
| WO | WO 2009034386 A1 * | 3/2009 |
| WO | WO 2009/062059 | 5/2009 |
| WO | WO 2009/091031 | 7/2009 |
| WO | WO 2009/151910 | 12/2009 |
| WO | WO 2010/018133 | 2/2010 |
| WO | WO 2010/033074 | 3/2010 |

OTHER PUBLICATIONS

Chavarot et al., "Synthesis of an Adenine-Pyridinaldoxime-Acridine Conjugate for Recognition of Abasic Site Lesions in DNA," Tetrahedron 1997, 53(40): 13749-13756.

Dvorakova et al., "Synthesis of 2'-aminomethyl derivatives of N-(2-(phosphonomethoxy)ethyl) nucleotide analogues as potential antiviral agents," J. Med. Chem., 1996, 39(17): 3263-3268.

Hirota, K et al., "Discovery of 8-hydroxyadenines as a Novel Type of Interferon Inducer," J. Med. Chem., 2002, 45(25): 5419-5422.

Holy et al., "Studies on S-adenosyl-L-homocysteine hydrolase. XVI. 9-(Aminoalkyl)-8-hydroxyadenines: preparation mechanism of formation, and use in affinity chromatography of S-adenosyl-L-homocysteine hydrolase," Collection of Czechoslovak Chemical Communications, 1986, 51(2), 459-77.

Isobe et al., "Synthesis and Biological Evaluation of Novel 9-Substituted-8-Hydroxyadenine Derivatives as Potent Interferon Inducers," J. Med. Chem., 2006 ; 49 (6); 2088-2095.

Isobe et al., "Synthesis and evaluation of 2-substituted 8-hydroxyadenines as potent interferon inducers with improved oral bioavailabilies," Bioorganic & Medicinal Chemistry, 2003, 11(17): 3641-3647.

Itahara et al., "Control of Liquid-Crystalline Properties by Base Pairing Adenine and Thymine," ChemPhysChem., 2002, 3(4): 378-379.

Kurimoto et al., "Prodrugs of 9-Benzyl-8-hydroxy-2-(2-hydroxyethylthio)adenine: Potent Interferon Inducing Agents in Monkeys," Chemical & Pharmaceutical Bulletin, 2004, 52(4): 466-469.

Kurimoto et al., "Synthesis and biological evaluation of 8-oxoadenine derivatives as Toll-like Receptor 7 agonists introducing the antedrug concept," J. Med Chem., 2010, 53:2964-2972.

Kurimoto et al., "Synthesis and evaluation of 2-substituted 8-hydroxyadenines as potent interferon inducers with improved oral bioavailabilies," Bioorganic & Medicinal Chemistry, 2004, 12(5): 1091-1099.

Kurimoto et al., "Synthesis and Structure—Activity Relationships of 2-Amino-8-hydroxyadenines as Orally Active Interferon Inducing Agents," Bioorganic & Medicinal Chemistry, 2003, 11(24): 5501-5508.

Spassova et al., "Synthesis of N-(3-Azido-2-Hydroxypropyl), N-(3-Phthalimido-2-Hydroxypropyl) and N-(3-Amino-2-Hydroxypropyl) Derivatives of Heterocyclic Bases," Collection of Czechoslovak chemical Communications, 1994, 59(5): 1153-1174.

European Search Report dated Mar. 31, 2011 in corresponding European application 09703040.7.

Aoki et al., "Weekly Dosing of AZD8848/DSP-3025, a Novel TLR7 Agonist Antedrug, Demonstrates a Prolonged Period of Control Against Markers of Pulmonary Inflammation in an Allergen Challenge Model in the Mouse," ATS New Orleans, May 2010.

Bell et al., "AZD8848/DSP-3025, a Novel Potent TLR7 Agonist Antedrug, Demonstrates Negligible Systemic Activity and a Prolonged Period of Control After Cessation of Weekly Dosing in a Brown Norway Rat Ovalbumin Challenge Model," ATS New Orleans, May 2010.

Biffen et al., "Biological Activity of a Novel TLR7 Agonist Antedrug for the Treatment of Allergic Diseases," ATS New Orleans, May 2010.

Biffen et al., "Novel TLR7 Agonists for the Treatment of Allergic Diseases," Toll 2011, Riva del Garda, Italy, May 4-7, 2011—Abstract.

(56) References Cited

OTHER PUBLICATIONS

Biffen et al., "Biological Characterization of a Novel Class of Toll-Like Receptor 7 Agonists Designed to Have Reduced Systemic Activity," Br J Pharmacol, 2012, 166: 573-586.

Eiho et al., "Mechanism of Long-Lasting Suppression Against Th2 Immune Response in the Lung by a Novel Antedrug TLR7 Agonist," European Respiratory Society, Amsterdam, Sep. 24-28, 2011—Abstract.

Eiho et al., "Mechanism of Long-Lasting Suppression Against Th2 Immune Response in the Lung by a Novel Antedrug TLR7 Agonist," European Respiratory Society, Amsterdam, Sep. 24-28, 2011—Poster.

English-language translation of Chinese Official Action dated Sep. 5, 2012, in corresponding Chinese application 200980109466.2.

European Examination Report dated Jan. 13, 2012, in corresponding European application 09703040.7.

Greiff et al., "Repeated Intranasal TLR7 Stimulation Reduces Allergen Responsiveness in Allergic Rhinitis," European Respiratory Society. Amsterdam, Sep. 24-28, 2011—Abstract.

Greiff et al., "Repeated Intranasal TLR7 Stimulation Reduces Allergen Responsiveness in Allergic Rhinitis," European Respiratory Society. Amsterdam, Sep. 24-28, 2011—Poster.

Ikeda et al., "AZD8848/DSP-3025, a Novel Potent TLR7 Agonist Antedrug, Demonstrates Efficacy Against Airway Obstruction and Other Inflammatory Endpoints in Guinea Pig Models of Rhinitis and Asthma With Acute and Weekly Dosing," ATS New Orleans, May 2010.

Matsui et al., "Mechanisms of Inhibition of Type-2 Cytokines by Novel TLR7 Agonist Antedrugs," ATS New Orleans, May 2010.

McInally et al.. "Identification of a Novel TLR7 Agonist Antedrug," EFMC-ISMC 201, Brussels, Belgium, Sep. 5-9, 2010.

Tojo et al., "Synthesis and Biological Evaluation of a Novel TLR7 Agonist With an Antedrug Strategy," EFMC-ISMC 201, Brussels, Belgium, Sep. 5-9, 2010.

* cited by examiner

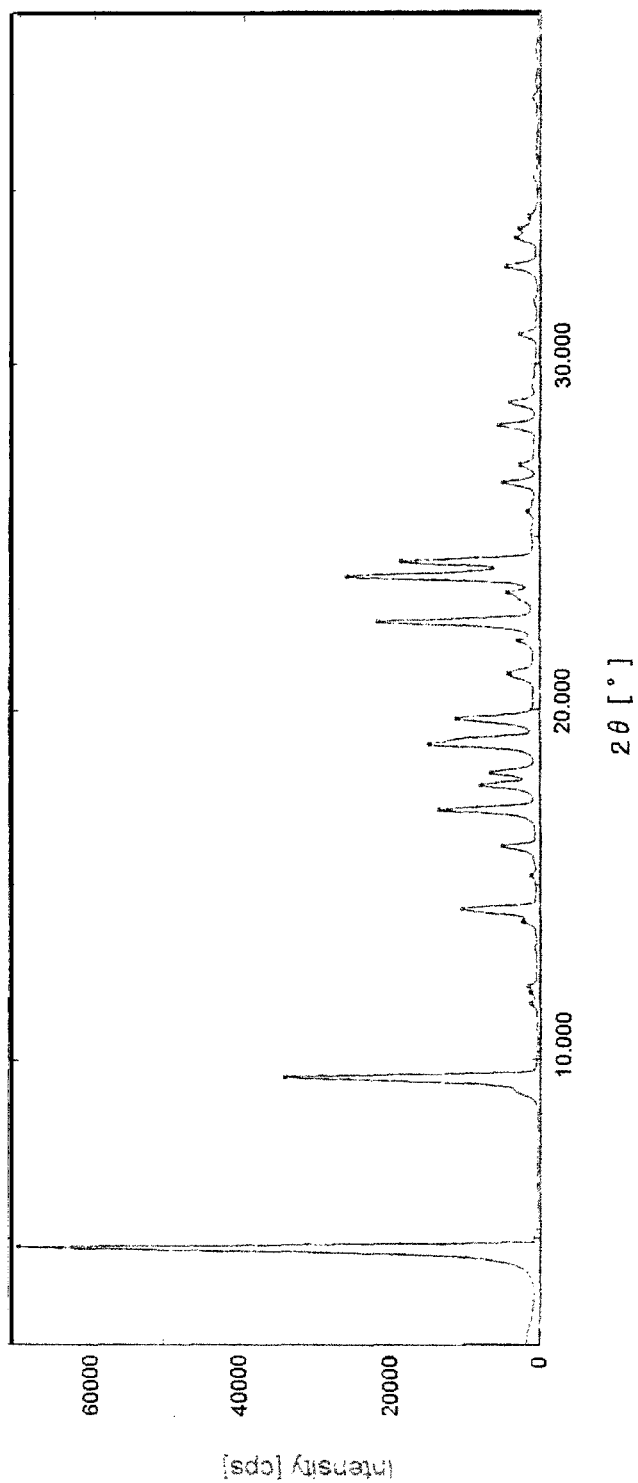

METHOD FOR PREPARING ADENINE COMPOUND

RELATED APPLICATIONS

The present application is a U.S. National Phase Application of International Application No. PCT/JP2009/050550, filed Jan. 16, 2009, which claims the benefit of Japanese Patent Application No. JP 2008-007974, filed Jan. 17, 2008, both of which are hereby incorporated by reference in their entirety.

The subject matter claimed in this application was made as a result of activities undertaken within the scope of a joint research agreement dated Dec. 19, 2003 between AstraZeneca AB and Sumitomo Pharmaceuticals Co. Ltd. All the rights and obligations of Sumitomo Pharmaceuticals Co. Ltd. as defined in the joint research agreement between AstraZeneca AB and Sumitomo Pharmaceuticals Co. Ltd. were assumed by Dainippon Sumitomo Pharma Co. Ltd., a company created by the merger of Dainippon Pharmaceutical Co. Ltd. and Sumitomo Pharmaceuticals Co. Ltd. effective Oct. 3, 2005.

TECHNICAL FIELD

The present invention relates to a method for preparing an adenine compound useful as a medicament, and to an intermediate for preparing it.

BACKGROUND OF ART

An adenine compound represented by the following formula (1):

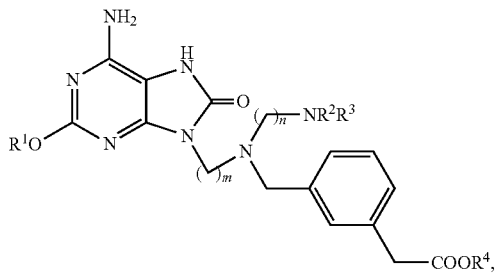

(1)

wherein m, n, $R^1$, $R^2$, $R^3$ and $R^4$ are the same as defined below, or a pharmaceutically acceptable salt thereof is known to be useful as a medicament (See patent documents 1 and 2).

It is described in patent document 1 that methyl (3-{[[3-(6-amino-2-butoxy-8-oxo-7,8-dihydro-9H-purine-9-yl)propyl](2-morpholin-4-ylethyl)amino]methyl}phenyl)acetate is prepared by reacting 9-(3-aminopropyl)-2-butoxy-8-methoxy-9H-purine-6-amine with methyl 3-formylphenyl acetate, and then alkylating the reacted compound with 2-morpholinoethyl chloride, followed by treating with an acid, and so on.

Furthermore, it is described in patent document 1 that methyl (3-{[[4-(6-amino-2-butoxy-8-oxo-7,8-dihydro-9H-purine-9-yl)butyl](3-morpholin-4-ylpropyl)amino]methyl}phenyl)acetate is prepared by reacting 9-(4-bromobutyl)-2-butoxy-8-methoxy-9H-purine-6-amine with N-(3-aminopropyl)morpholine, and treating the reacted product with an acid, followed by alkylation with methyl 3-bromomethylphenylacetate, and so on.

Furthermore, it is described in patent document 2 that methyl (3-{[[3-(6-amino-2-butoxy-8-oxo-7,8-dihydro-9H-purine-9-yl)propyl](3-dimethyaminopropyl)amino]methyl}phenyl)acetate is prepared by treating 9-(3-bromopropyl)-2-butoxy-8-methoxy-9H-purine-6-amine with an acid, and then reacting it with 3-hydroxypropylamine, methyl 3-bromomethylphenylacetate, mesyl chloride and dimethylamine, successively, and so on.

However, according to these methods, in case of an alkylation step by substitution reaction with a primary amine and an alkyl halide, or by reductive amination of an aldehyde, there is a problem that not only an objective monoalkylated compound but also dialkylated compound, a by-product is produced. Furthermore, in case of the above formula (1) wherein m is 3 or 4, there is a possibility to produce a tricyclic compound bridged between positions 9 and 8 of the purine nucleus, or between positions 9 and 3 of the purine nucleus or a by-product derived from β-elimination.

Furthermore, in case of a compound having an leaving group such as 9-(3-bromopropyl)-2-butoxy-8-methoxy-9H-purine-6-amine, etc., there is a problem (possibility) to produce a by-product represented by the following formula (11) which are formed by condensation of two molecules.

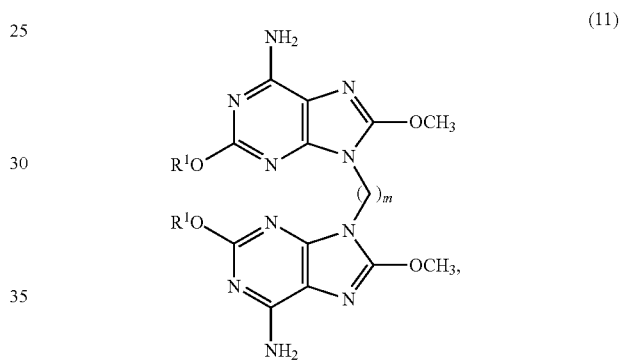

(11)

wherein m and $R^1$ is the same as define below.

As mentioned above, a method for preparing a compound represented by the formula (1) which is produced in a high yield with controlling a production of by-products has been desired.

Patent document 1: WO 2005/092893 gazette

Patent document 2: WO 2007/031726 gazette

DISCLOSURE OF THE INVENTION

Problem to be Solved by the Invention

Problem to be solved by the invention is to provide a novel method for preparing an adenine compound represented by the formula (1) and a pharmaceutically acceptable salt thereof which is useful for a medicament, and an intermediate for preparing it.

Means for Solving the Problem

The present inventors have been extensively studied for establishment for a novel method for preparing an adenine compound represented by the formula (1) or a pharmaceutically acceptable salt thereof and as a result the present invention has been completed.

Namely the present invention relates to

[1] a method for preparing a compound represented by the following formula (1):

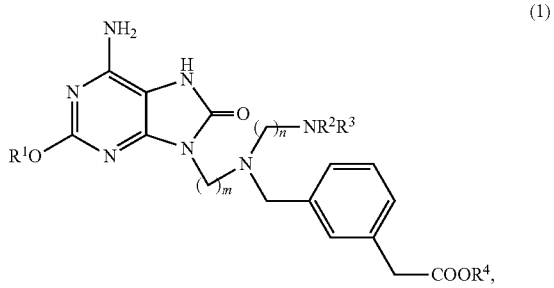
(1)

wherein m and n are independently an integer of 2 to 5, $R^1$ is $C_{1-6}$ alkyl group, $R^2$ and $R^3$ are the same or different, and hydrogen atom, or $C_{1-6}$ alkyl group, or $R^2$ and $R^3$ are combined with an adjacent nitrogen atom to form pyrrolidine, morpholine, thiomorpholine, piperidine, homopiperidine, piperazine or homopiperazine, and nitrogen atom of position 4 of said piperazine or homopiperazine may be substituted by $C_{1-4}$ alkyl group, and $R^4$ is $C_{1-3}$ alkyl group, or its pharmaceutically acceptable salt, which is characterized by reacting a compound represented by the following formula (2):

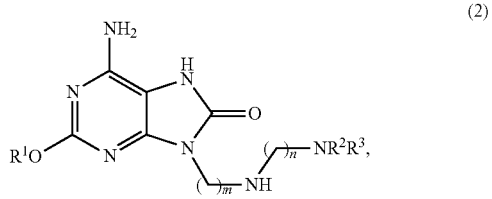
(2)

wherein m, n, $R^1$, $R^2$ and $R^3$ are the same as defined in above formula or its salt and a compound represented by the following formula (3):

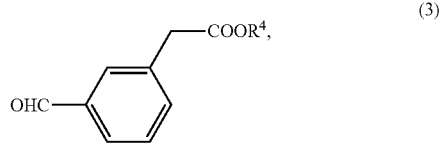
(3)

wherein $R^4$ is the same as defined in above formula (1), in the presence of a boron-containing reducing agent.

Effect of Invention

According to the present invention, it has become possible to provide a novel method for preparing an adenine compound represented by the formula (1) or a pharmaceutically acceptable salt thereof which is useful as a medicament. According to the present invention, the production of a by-product is smaller and the objective compound is prepared in a higher yield comparing with known methods.

BRIEF EXPLANATION OF FIGURE

FIG. 1 shows XRPD data on compound of Example 5.

THE BEST MODE FOR CARING OUT THE PRESENT INVENTION

The present invention is explained more in detail below.

In the present specification, "$C_{1-6}$ alkyl group" includes $C_{1-6}$ straight or branched alkyl group, such as methyl group, ethyl group, propyl group, isopropyl group, butyl group, pentyl group, hexyl group, etc.

In the present specification, "$C_{1-3}$ alkyl group" includes methyl group, ethyl group, propyl group and isopropyl group.

In the present specification, m and n are independently preferably an integer of 2 to 4, more preferably 3.

In the present specification, $R^1$ is preferably $C_{3-5}$ straight alkyl group, more preferably butyl group.

In the present specification, $R^2$ and $R^3$ are preferably the same or different, and $C_{1-4}$ alkyl group, or $R^2$ and $R^3$ are preferably combined with an adjacent nitrogen atom to form pyrrolidine, morpholine, thiomorpholine, piperidine, homopiperidine, piperazine or homopiperazine. Nitrogen atom of position 4 of said piperazine or homopiperazine may be substituted by $C_{1-4}$ alkyl group. More preferably $R^2$ and $R^3$ are combined with an adjacent nitrogen atom to form a morpholine.

In the present specification, $R^4$ is preferably methyl group.

In the present specification, a compound represented by the formula (1) or its pharmaceutically acceptable salt, and its intermediate or a salt thereof include hydrate and/or solvate thereof.

Furthermore, a compound represented by the formula (1) or its pharmaceutically acceptable salt, and its intermediate or a salt thereof may form a tautomer, if any and a tautomer thereof is included in the present invention.

In the present invention, the salt of the compound represented by the formula (2):

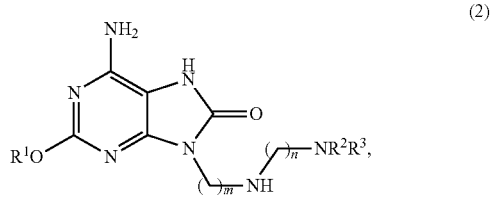
(2)

wherein m, n, $R^1$, $R^2$ and $R^3$ are the same as defined in above formula (1), is not specifically limited, but includes a salt which is commonly used in the art, such as hydrochloride, hydrobromide, maleate, fumarate, malonate, oxalate, trifluoroacetate, etc., preferably hydrochloride, maleate, fumarate, or malonate.

A boron-containing reducing agent used in condensation reaction of a compound represented by the formula (2) with a compound represented by the formula (3):

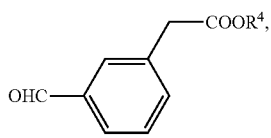

(3)

wherein R⁴ is the same as defined in above formula (1), includes sodium triacetoxyborohydride, sodium cyanoborohydride, dimethylsulfideboron complex, 2-pycolin-boron complex, etc., preferably sodium triacetoxyborohydride, sodium cyanoborohydride, more preferably sodium triacetoxyborohydride.

The above reaction can be conducted in the presence or absence of a base. In case of a salt of compound (2), an appropriate amount of a base may be used in order to produce a free amino group. For example, a base may be added 0 to 4, preferably 2 to 3 mole equivalents to compound (2). The base includes for example, a tertiary amine such as triethylamine, diisopropylethylamine, N-methymorpholine, 4-(N,N-dimethyamino)pyridine, etc., preferably triethyamine.

The reaction temperature is not specifically limited, but is usually 15 to 40° C., preferably 20 to 30° C.

The reaction solvent is not specifically limited, but is N-methylpyrrolidone (NMP), dimethy sulfoxide (DMSO), N,N-dimethylormamide (DMF), dichloromethane, tetrahydrofuran (THF), etc., preferably N-methylpyrrolidone (NMP). Especially in case of using triethylamine as a base, NMP as a solvent is preferably used.

The reaction time is usually 3 to 24 hours.

The order that starting materials and agents are added in the above reaction is not specifically limited, but it is preferable that the substances are added in the order that (i) an amine compound (2), (ii) a base such as triethylamine, etc., (iii) a boron-containing reducing agent, and then (iv) an aldehyde compound (3) for controlling the production of a by-product represented by the following formula (12):

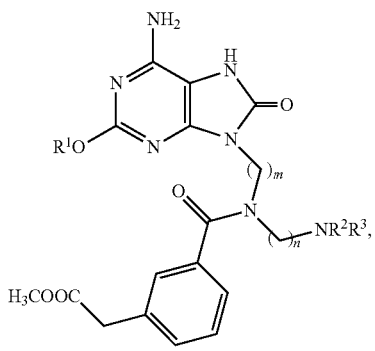

(12)

wherein m, n, R¹, R² and R³ are the same as defined in above formula (1).

Compound (1) can be isolated in a free form or a salt with an appropriate acid. The salt is not specifically limited as long as it is a pharmaceutically acceptable salt, but includes hydrochloride, sulfate, maleate, fumarate, hydrobromic acid salt, nitrate, orthophosphate, acetate, benzoate, methanesulfonate, ethanesulfonate, L-lactate, aspartate, 2-naphthalenesulfonate, citrate, 1,5-naphthalenedisulfonate, succinate, etc.

As a preferable embodiment of compound (1), the compound (methyl (3-{[[3-(6-amino-2-butoxy-8-oxo-7,8-dihydro-9H-purine-9-yl)propyl](3-morpholin-4-ylpropyl)amino]methyl}phenyl)acetate) prepared by Example 5 or 8 is illustrated. Said compound has a unitary crystal in purity of 80%, preferably 90%, more preferably 95% or more. The crystal shows characteristic values described in Table 1±0.2 as diffraction peaks at angle of diffraction 2θ (°) (measured by powder X-ray diffraction) and if a crystal is consistent with 5 or more, preferably 10 or more peaks among peaks shown in Table 1, the crystal can be identified to be the same.

Furthermore, the present invention relates to

[2] a method for preparing compound (1) set forth in above [1], wherein the method contains further process for preparing compound (2) or its salt consisting of following steps (a) to (c):

Step (a) for preparing a compound represented by formula (5):

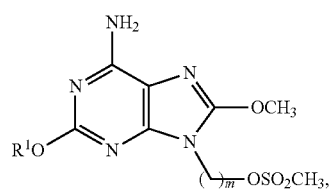

(5)

wherein m and R¹ is the same as defined in above formula (1), which comprises reacting a compound represented by formula (4):

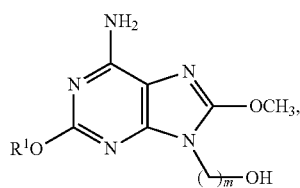

(4)

wherein m and R¹ is the same as defined in above formula (1), and methanesulfonyl chloride in the presence of a base;

Step (b) for preparing a compound represented by formula (7):

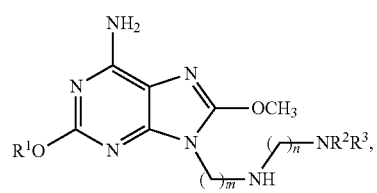

(7)

wherein m, n, R¹, R² and R³ are the same as defined in above formula (1), or its salt which comprises reacting a compound prepared by step (a) with a compound represented formula (6):

$$H_2N \underset{n}{\underbrace{\phantom{XXX}}} NR^2R^3, \quad (6)$$

wherein m, n, R$^1$, R$^2$ and R$^3$ are the same as defined in above formula (1), or its salt; and then, Step (c) for preparing compound (2) or its salt which is prepared by treating compound prepared by step (b) with an acid.

Each step is explained in detail below.

In step (a), compound (4) is usually methanesulfonylated with methanesulfonyl chloride to prepare compound (5).

Methanesulfonylation is usually in the presence of a base, such as a tertiary amine like triethylamine, diisopropylethylamine, N-methymorpholine etc., preferably triethylamine or diisopropylethylamine.

Amount of methanesulfonyl chloride used in this reaction is 1 to 2 mole equivalents, preferably 1 to 1.3 mole equivalents to compound (4).

Further more, trimethylamine hydrochloride can be used as an agent for preventing a by-product, and dimethyaminopyridine can be used as a reaction promoting agent.

The reaction temperature is around 0° C. to 40° C., preferably around 0° C. to 15° C.

The reaction solvent is not specifically limited, but includes N-methypyrrolidone, dimethyl sulfoxide, dimethylformamide, tetrahydrofuran, etc.

The reaction time is usually 10 to 60 minutes.

After completion of the reaction, to the reaction mixture is added water in order to crystallize the objective compound to give compound (5).

Furthermore, when compound (5) is heated, it produces following compounds (13) and (14):

(13)

(14)

wherein m and R$^3$ the same as defined in above formula (1), and m is an integer 1 to 3.

Therefore, after compound (5) is dried at 0° C. to 40° C., preferably 0° C. to 20° C., more preferably is not dried, compound (5) is subjected to next reaction step.

Step (b):

As explained above, in a known method for preparing compound (7) by reacting primary amine (6) and alkyl halide, etc., there is a problem (possibility) that dialkylated compound or tricyclic compound is produced as a by-product. For example, when alkyl halide carrying such a leaving group as chlorine atom which is less reactive is used, heating (about 60° C.) is required. Therefore, there is a possibility to produce a by-product under such a condition. For example, in case of compound (7) wherein m is 2 or 3, there is a possibility to produce as a by-product, a following cyclized compound represented by formula (15)

(15)

wherein m, n, R$^1$, R$^2$ and R$^3$ are the same as defined in above formula (1).

Furthermore, when alkyl halide carrying such a leaving group as bromine atom which is highly reactive is used, there is a possibility to produce as a by-product, a bis-adenine compound represented by the following formula (16):

(16)

wherein m, n, R$^1$, R$^2$ and R$^3$ are the same as defined in above formula (1).

However, in case of methanesulfonyloxy group (mesyl group) as a leaving group, mesyl group on compound (5) shows highly reactivity, and in spite of the fact that the reaction is carried out at room temperature (about 5° C. to 35° C.), the production of a by-product is controlled to give compound (7) in a good yield.

Furthermore, when compound (6) is used 2 to 30, preferably 10 to 15 mole equivalents to compound (5), a starting material, the production of bis-adenine compound (16) mentioned above can be controlled.

This reaction can be carried out in the presence of a reaction auxiliary or assistant such as sodium bromide, potassium bromide, sodium iodide, etc.

N-Methylpyrrolidone or dimethy sulfoxide may be used as a reaction solvent, if necessary, but compound (6) is usually used in excess and served as a solvent. Namely compound (6) is usually used in excess to compound (5), for example, about 2 to 30, preferably 15 mole equivalents to compound (5) to be able to control the production of a by-product.

The reaction temperature is preferably about 20 to 35° C.

The reaction time is usually 6 to 24 hours.

Compound (6) used as a starting material is known and the commercially available product or the product which is prepared in accordance with the similar manners as known by a skilled person in the art can be used.

After the reaction, compound (6) can be removed by extraction. For example, the desired compound can be extracted with a mixture of toluene and THF, or with chloroform.

The extract can be subjected to next reaction without condensation, but the desired compound can be isolated in a form of its salt with other acid by a conventional method. The acid is preferably trifluoroacetic acid, maleic acid, or malonic acid.

Step (c)

As an acid used in a process for converting compound (7) into compound (2), is illustrated a strong acid such as hydrochloric acid, hydrobromic acid, sulfuric acid, methanesulfonic acid, toluenesulfonic acid, preferably hydrochloric acid, hydrobromic acid, more preferably 12 to 40% hydrochloric acid.

The reaction temperature is preferably about 0 to 0° C.

The reaction in this step can be carried out without solvent, but usually after dissolving compound (7) in a suitable organic solvent, to the solution is added the acid.

The organic solvent is not specifically limited as long as compound (7) is dissolved therein, but is preferably toluene, tetrahydrofuran or a mixture thereof, such as a mixture of toluene and tetrahydrofuran.

The acid can be used, if necessary after dissolving it in water or an organic solvent. For example, in case of hydrochloric acid or hydrobromic acid, the acid may be further diluted with water or may be dissolved in an organic solvent such as ethanol or dioxane.

The reaction temperature is usually 0° C. to 40° C., preferably about 25° C.

The reaction time is usually 1 to 5 hours.

Without concentrating the reaction mixture obtained in the above step (b) thereto is usually added the acid, or to a solution containing compound (7) extracted from the reaction mixture is added the acid to prepare compound (2).

As compound (2) is superior in thermal stability, after the reaction solvent is removed in vacuo under heating after the reaction, the residue is recrystallized from a mixture of isopropyl alcohol and methanol and filtrated to prepare compound (2) in high purity.

Compound (2) is obtained in a salt with an acid used in step (c), but the salt may be exchanged into a salt with other acid if necessary in accordance with a known method. For example, to a salt of compound (2) obtained in step (c) is added a base such as sodium carbonate, etc., to produce a free form, and then, an acid is added to the free form, or by a method that to the reaction mixture of step (c) is added other acid to isolate as a salt with other acid.

When a salt of compound (2) is highly hygroscopic or said acid forms a hardly soluble salt with a base which is used in next step, the salt of compound (2) is preferably exchanged with a salt with other acid. Preferable salts of compound (2) are maleate, fumarate and malonate.

Furthermore, the present invention relates to

[3] a method for preparing compound (1) or its pharmaceutically acceptable salt set forth in above [2] wherein the method contains further process for preparing compound (4) or its salt consisting of the following steps (d) to (e):

Step (d) for preparing a compound represented by formula (10):

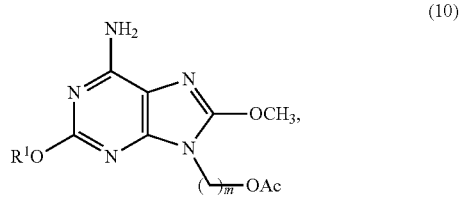

wherein Ac is acetyl group, m and $R^1$ is the same as defined in above formula (1), which comprises reacting a compound represented by formula (8):

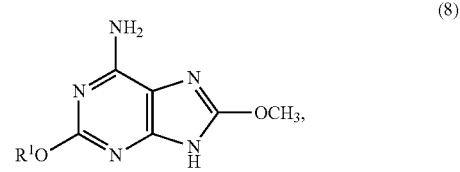

wherein $R^1$ is the same as defined in above formula (1), and a compound represented by formula (9):

wherein m is the same as defined in above formula (1), in the presence of a base, and then Step (e) for preparing a compound represented by formula (4):

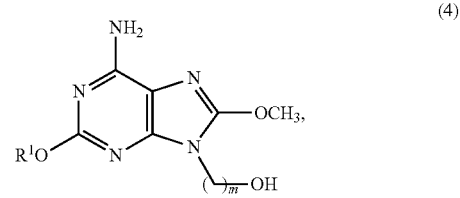

wherein m and $R^1$ are the same as defined in above formula (1), which comprises hydrolyzing a compound prepared in step (d).

Steps (d) and (e) are explained in detail below.

Step (d)

In step (d) condensation reaction of compound (8) and compound (9) is usually carried out in the presence of a base, such as an inorganic base like potassium carbonate, or sodium carbonate.

The compound (9) is used 1 to 2, preferably 1 to 1.3 mole equivalents to compound (8).

The reaction temperature is about 20 to 40° C.

A reaction solvent is not specifically limited, but is N-methylpyrrolidone, dimethyl sulfoxide, or dimethylformamide.

The reaction time is usually 2 to 8 hours.

Compound (10) produced in this reaction can be isolated or can be subjected to next reaction step without isolation.

Furthermore, compound (8) and compound (9) which are used as a starting material are known and can be commercially available or prepared in accordance with a method known by a skilled person in the art.

Step (e)

In step (e), hydrolysis can be carried out in accordance with hydrolysis of ester known by a skilled person in the art. For example, the hydrolysis is carried out by using alkali metal hydroxide such as sodium hydroxide, or potassium hydroxides.

The reaction temperature is about 20 to 70° C.

The reaction solvent is not specifically limited, but a conventional organic solvent in the art used in ester hydrolysis can be used. The hydrolysis can be also carried in an aqueous solution of alkali metal hydroxide without using an organic solvent. Example of the solvent is water-alcohol, preferably methanol-water.

The reaction time is usually 1 to 5 hours.

[4] Compounds represented by following formula (2), (4), (5), (7) or (10) which are used as an intermediate in the above reactions:

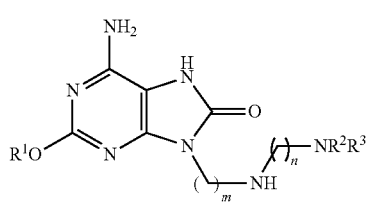
(2)

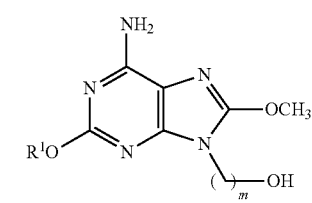
(4)

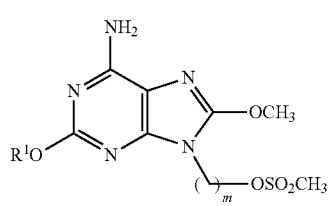
(5)

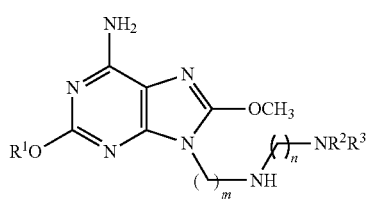
(7)

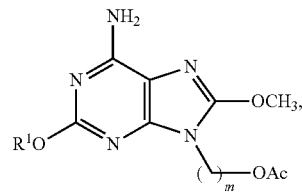
(10)

wherein Ac is acetyl group, m, n, $R^1$, $R^2$ and $R^3$ are the same as defined in above formula (1) are novel, and the present invention includes these compounds, a salt, a hydrate, and a solvate thereof.

Furthermore, a tautomer of compound (2) is included in the present invention.

Compound (2) or (7) can form its salt, and its salt is not specifically limited, but includes a conventional salt such as hydrochloride, hydrobromide, maleate, fumarate, oxalate, malonate, trifluoroacetate, etc.

Furthermore, compound (3) which is used as a starting material in the present invention, is prepared according to the following reaction scheme:

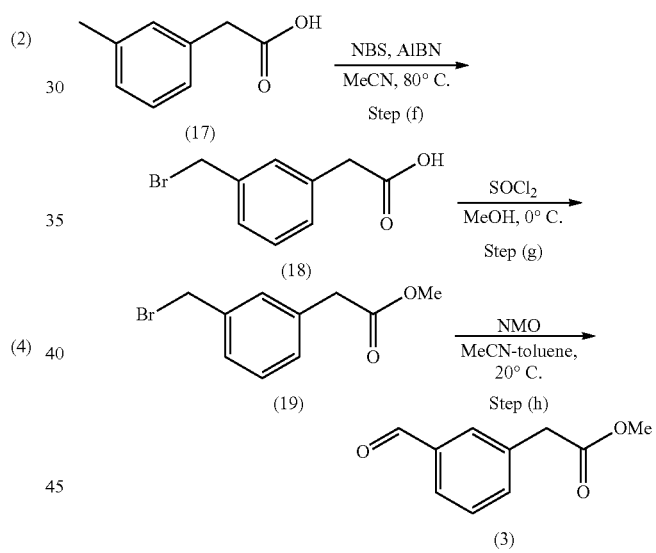

Each step is explained in detail below.

Step (f)

3-Bromomethylphenylacetic acid is prepared by brominating methyl group of 3-methyphenylactetic acid with NBS (N-bromosuccinimide). AIBN (α,α'-azobisisobutyronitrile) is used as a free-radical initiator.

The reaction solvent is not limited, but includes a halogenated compound such as carbon tetrachloride, ethylacetate or acetonitrile, preferably acetonitrile.

In this step, a by-product can be removed by crystallization and for example, anhydrous butyl acetate is used as the solvent for crystallization.

Step (g)

3-Bromomethyphenylacetic acid obtained in step (f) is converted into methyl ester in accordance with a method described in examples or a method known by a skilled person in the art.

Step (h)

Methyl 3-bromomethyphenylacetate is oxidized with NMO (4-methymorpholine-N-oxide) to prepare an aldehyde compound. The amount of NMO is usually 1 to 10, preferably 2 to 3 mole equivalents to methyl 3-bromomethyphenylacetate. The solvent is not specifically limited, but includes a polar solvent such as acetonitrile, DMSO and a mixture of a polar solvent an a non-polar solvent, preferably a mixture of acetonitrile and toluene.

Compound (3) is prepared as mentioned above.

The present invention is explained by following examples, but the invention is not limited by them.

In the following examples, the commercially available reaction agents and solvents were used. Organic solutions were dried over anhydrous sodium sulfate unless there is a specific definition.

Chemical shift of $^1$H NMR was reported on the basis of inner standard tetramethysilan.

"Me" means methyl group, "TFA" means trifluoroacetic acid, and "Ms" means methanesulfonyl group in following formulas.

Conditions of HPLC on analysis for purity are as follows:
Reverse HPLC column: Mightysil RP-18 GP (5 μm, 4.6 mm φ×150 mm),
Column temperature: 40° C.,
Flow rate: 1.0 ml/min,
UV wavelengths: 254 nm,
Mobile phase: A solution aqueous 0.1% TFA-water, B solution acetonitrile (10%-100%/21 min gradient concentration)

Melting point was measured by SC/DSC: Sealed Cell/Differential Scanning calorimetry, namely DSC6200R (by Seiko-Instrument) sample holder:
SUS sealed Cell, under following conditions:
Heat-up rate: 10° C./min., Nitrogen gas circumstance (flow rate 60 mL/ml),
Measuring range; −20° C.~560° C.,
Sample; 2.01 mg, aluminum oxide: 2.31 mg as a referential compound Powder X-ray diffraction (XRPD) was measure with RINT2500V (Riken) under following conditions: diffraction angle 2θ; 4° to 40° CuKα radiation (focusing optics), X-ray: 50 kV-300 mA, Scanning θ-2θ, Scanning speed θ=4.0/min., Scanning interval: 2θ=0.02°, measuring angle range 2θ=2~40°, Dispersion slit: −1/2°, Emission slit: −0.15 mm, Scattering slit: −1/2°.

EXAMPLE 1

3-(6-Amino-2-butoxy-8-methoxy 9H-yl)propan-1-ol

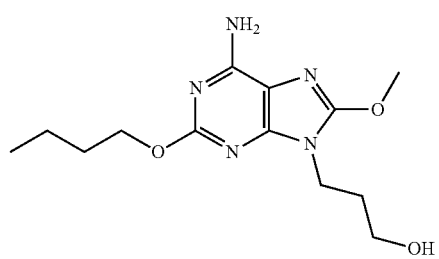 [SMILES: CCCCOc1nc(N)c2nc(OC)n(CCCO)c2n1]

To a suspension of 2-butoxy-8-methoxy-9H-purine-6-amine trifluoroacetate (20.00 g, 56.93 mmol) in NMP (111.24 g), were added water (1.65 g) and potassium carbonate (23.61 g, 170.80 mmol). Further 3-acetoxypropyl bromide (12.37 g, 68.32 mmol) was added thereto, followed by stirring for 3 hours at 30° C. To the reaction mixture were added methanol (79.10 g) and 2% aqueous sodium hydroxide solution (100 g), and the mixture was stirred for 3 hours at 70° C. After adding water (200 g), the mixture was cooled to 7° C. and the resulting crystal was filtered and dried to give the subject compound (13.03 g, 77.5%). Purity: 99.46% (HPLC)

$^1$H NMR (DMSO-d$_6$) δ 6.77 (2H, bs), 4.57 (1H, t, J=5.2 Hz), 4.16 (2H, t, J=6.6 Hz), 4.04 (3H, s), 3.89 (2H, t, J=7.4 Hz), 3.42-3.38 (2H, m), 1.85-1.78 (2H, m), 168-1.61 (2H, m), 1.44-1.35 (2H, m), 0.92 (3H, t, J=7.3 Hz).

EXAMPLE 2

3-(6-Amino-2-butoxy-8-methoxy-9H-purin-9-yl) propyl methanesulfonate

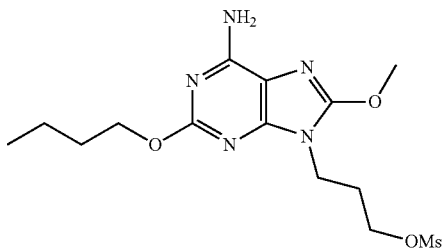 [SMILES: CCCCOc1nc(N)c2nc(OC)n(CCCOS(C)(=O)=O)c2n1]

To a solution of 3-(6-amino-2-butoxy-8-methoxy-9H-purin-9-yl)propan-1-ol)(12.00 g, 40.63 mmol) in NMP (97.45 g) was added triethyamine (6.17 g, 90.65 mmol) and the mixture was cooled to 5° C. Thereto was dropped methanesulfonyl chloride (6.05 g, 52.82 mmol) and the mixture was stirred at 5° C. for 30 minutes, followed by adding a water (244.00 g). After stirring for 1 hour, the resulting crystal was filtered to give the subject compound (30.34 as a crude product). Purity: 98.39% (HPLC)

EXAMPLE 3

6-Amino-2-butoxy-9-{3-[(3-morpholin-4-ylpropyl) amino]propyl}-7,9-dihydro-8H-purine-8-one trihydrochloride

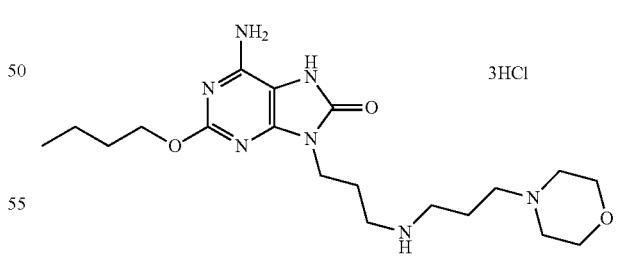

To N-(3-aminopropyl)morpholine (86.90 g, 602.52 mmol) which was cooled to 3° C. was in several times added 3-(6-amino-2-butoxy-8-methoxy-9H-purin-9-yl)propyl methanesulfonate (amount corresponding to dried weight 15.00 g (40.17 mmol)) not to exceed to 20° C. After stirring at 28° C. for 10 hours, thereto was added 15% brine (160.00 g), and the mixture was extracted with a mixture of toluene (194.08 g) and THF (199.8 g). After removal of the organic solvent, concentrated hydrochloric acid (41.84 g) was added thereto, and the mixture was stirred at 25° C. for 3 hours. After removal by distillation of the solvent, to the residue was added methanol (118.65 g), followed by raising to 55° C. Isopropanol (353.25 g) was dropped thereto and the mixture was crystallized and further raised to 70° C. After one hour, the mixture was cooled to 20° C. The resulting crystal was filtered, washed and dried to give the subject compound (16.80 g, 77.5% by 2 steps). Purity: 99.70% (HPLC)

$^1$H NMR (DMSO-$d_6$) δ 11.12 (1H, bs), 10.58 (1H, bs), 8.93 (2H, bs), 4.20 (2H, t, J=6.6 Hz), 3.97-3.94 (2H, m), 3.84-3.74 (4H, m), 3.40 (1H, bs), 3.38 (1H, bs), 3.19-3.14 (2H, m), 3.07-2.92 (6H, m), 2.10-1.91 (4H, m), 1.69-1.62 (2H, m), 1.45-1.35 (2H, m), 0.92 (3H, t, J=7.4 Hz).

EXAMPLE 4

6-Amino-2-butoxy-9-{3-[(3-morpholin-4-ylpropyl)amino]propyl}-7,9-dihydro-8H-purine-8-one dimaleate

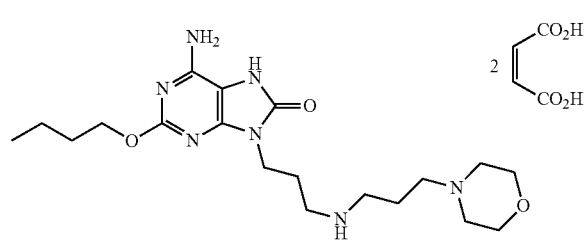 [SMILES: CCCCOc1nc(N)c2[nH]c(=O)n(CCCNCCCN3CCOCC3)c2n1 ; O=C(O)/C=C\C(=O)O]

To a solution of 6-amino-2-butoxy-9-{3-[(3-morpholin-4-ylpropyl)amino]propyl}-7,9-dihydro-8H-purine-8-one trihydrochloride (15.00 g, 29.02 mmol) in 10% brine (105.00 g) was added an aqueous 10% sodium carbonate to be neutralized. After adding chloroform (335.7 g), the mixture was heated to 53° C., and the aqueous layer was separated and removed. After an organic layer was concentrated, to the residue was added methanol (296.63 g) and the mixture was raised to 50° C. After methanol (59.33 g) containing maleic acid (6.74 g, 58.04 mmol) was dropped, a white crystal was confirmed. After stirring at 70° C. for 1 hour, the mixture was cooled to 5° C., a crystal was filtered, washed and dried to give the subject compound (17.60 g, 94.8%). Purity: 99.62% (HPLC)

$^1$H NMR (DMSO-$d_6$) δ 9.95 (1H, bs), 8.36 (1.7H, bs), 6.48 (2H, bs), 6.08 (4H, s), 4.15 (2H, t, J=6.6 Hz), 3.77 (2H, t, J=6.5 Hz), 3.70 (4H, bs), 2.95 (4H, bt, J=7.2 Hz), 2.77 (6H, bs), 2.01-1.94 (2H, m), 1.86-1.80 (2H, m), 1.68-1.60 (2H, m), 1.44-1.35 (2H, m), 0.92 (3H, t, J=7.4 Hz).

EXAMPLE 5

Methyl (3-{[[3-(6-amino-2-butoxy-8-oxo-7,8-dihydro-9H-purin-9-yl)propyl](3-morpholin-4-ylpropyl)amino]methyl}phenyl)acetate

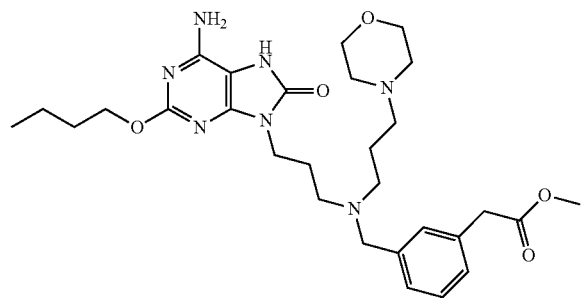 [SMILES: CCCCOc1nc(N)c2[nH]c(=O)n(CCCN(CCCN3CCOCC3)Cc3cccc(CC(=O)OC)c3)c2n1]

To a suspension of 6-amino-2-butoxy-9-{3-[(3-morpholin-4-ylpropyl)amino]propyl}-8-oxo-7,9-dihydro-8H-purine dimaleate (15.00 g, 23.45 mmol) in NMP (54.08 g) was added triethylamine (7.12 g, 70.35 mmol) at 25° C. Then sodium acetoxyborohydride (8.45 g, 39.87 mmol) was added thereto, followed by stirring at 25° C. for 15 minutes. After adding methyl (3-formylphenyl)acetate (6.27 g, 35.18 mol) and stirring at 25° C. for 8 hours, the mixture was cooled to 5° C. and then diluted with cold water (240.00). After adjusting pH to 7 with 10% sodium carbonate solution, a seed crystal was added thereto. After stirring for additional 15 minutes, the mixture was adjusted to pH 8 with 10% sodium carbonate solution and thereto was added water (15 g). After keeping at 5° C. for 1 hour, the resulting white solid was filtered, washed and dried to give the subject compound (12.10 g, 90.6%). The seed crystal used in the above was obtained by the method of the above example 5 without adding a seed crystal as the method of the above Example 5. Purity: 94.81% (HPLC)

$^1$H NMR (DMSO-$d_6$) δ 9.82 (1H, bs), 7.24-7.15 (3H, m), 7.10 (1H, d, J=7.3 Hz), 6.39 (2H, bs), 4.11 (2H, t, J=6.6 Hz), 3.67 (2H, t, J=7.2 Hz), 3.64 (2H, s), 3.59 (3H, s), 3.46-3.49 (6H, m), 2.41-2.34 (4H, m), 2.22-2.16 (6H, m), 1.85-1.80 (2H, m), 1.65-1.57 (2H, m), 1.52-1.45 (2H, m), 1.40-1.31 (2H, m), 0.89 (3H, t, J=7.4 Hz). m.p.: 152.7° C.

XRPD data on the subject compound is shown below.

TABLE 1

| 2θ (°) | d space (Å) | Rel Int (%) |
|---|---|---|
| 4.8 | 18.5 | 100 |
| 9.5 | 9.3 | 49 |
| 11.6 | 7.6 | 2 |
| 11.9 | 7.4 | 2 |
| 12.1 | 7.3 | 2 |
| 13.9 | 6.3 | 3 |
| 14.3 | 6.2 | 15 |
| 15.2 | 5.8 | 2 |
| 16.1 | 5.5 | 7 |
| 17.1 | 5.2 | 19 |
| 17.8 | 5.0 | 11 |
| 18.2 | 4.9 | 9 |
| 19.0 | 4.7 | 21 |
| 19.7 | 4.5 | 16 |
| 21.0 | 4.2 | 6 |
| 22.0 | 4.0 | 4 |

TABLE 1-continued

| 2θ (°) | d space (Å) | Rel Int (%) |
|---|---|---|
| 22.6 | 3.9 | 31 |
| 23.4 | 3.8 | 6 |
| 23.8 | 3.7 | 37 |
| 24.3 | 3.7 | 27 |
| 25.7 | 3.5 | 2 |
| 26.6 | 3.4 | 7 |
| 27.1 | 3.3 | 4 |
| 28.2 | 3.2 | 8 |
| 28.9 | 3.1 | 6 |
| 30.8 | 2.9 | 4 |
| 32.8 | 2.7 | 7 |
| 33.6 | 2.7 | 5 |
| 33.9 | 2.6 | 4 |
| 34.2 | 2.6 | 2 |

In above table, (2θ (°): Diffraction angle,
d space (Å): Space distance of crystal face,
Rel Int (%): Relative intensity, Accuracy - +/−0.1° 2θ: Deviation +/−0.1° 2θ)

EXAMPLE 6

Methyl (3-formylphenyl)acetate

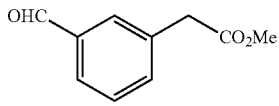 [SMILES: COC(=O)Cc1cccc(C=O)c1]

Step (i): [3-(Bromomethyl)phenyl]acetic acid

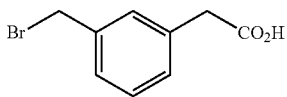 [SMILES: O=C(O)Cc1cccc(CBr)c1]

m-Tolylacetic acid (4.0 g, 26.64 mmol) and AIBN (α,α'-azobisisobutyronitrile) (0.044 g, 0.266 mmol) were dissolved in acetonitrile (11.9 g) and the solution was raised to 80° C. To this solution was dropped a solution of N-bromosuccinimide (4.98 g, 27.97 mmol) and AIBN (α,α'-azobisisobutyronitrile) (0.044 g, 0.266 mmol) in acetonitrile (32 g) for 1.5 hours. After stirring for 30 minutes the mixture was cooled to 50° C. and thereto was added butyl acetate (38.7 g). The mixture was concentrated to remove only acetonitrile. The resulting succinimide (crystal) was removed and the residue was washed three times with water. After concentrating to a desired concentration, thereto was added at 45° C. n-heptane (45.6 g) to produce a crystal. After cooling to 5° C., the crystal was filtered to give the sub-subject compound (3.76 g) as a white crystal. Yield: 62%

$^1$H NMR (CDCl$_3$) δ 7.34-7.33 (3H, m), δ 7.25-7.23 (1H, m), 4.49 (2H, s), 3.67 (2H, s).

Step (ii): Methyl [13-(bromomethyl)phenyl]acetate

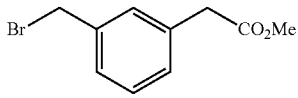 [SMILES: COC(=O)Cc1cccc(CBr)c1]

To a solution of compound (2.8 g, 12.22 mmol) obtained in step (i) in methanol (7 g) was added toluene (14 g) and the solution was cooled to 0° C. Thereto was dropped thionyl chloride (0.87 g, 7.33 mmol) and the mixture was stirred for 3 hours at 0° C. To a solution of sodium hydrogencarbonate (1.85 g, 12.22 mmol) in water (30.24 g) was added toluene (14 g). After cooled to 0° C., thereto was dropped the above reaction solution. The oil layer was washed with water (14 g), and the solvent was removed so as concentration of the solution becomes 25%. This solution was subjected to next step without purification.

$^1$H NMR (CDCl$_3$) δ 7.31-7.19 (4H, m), 4.48 (2H, s), 3.70 (3H, s), 3.64 (2H, s).

Step (iii): Methyl (3-formylphenyl)acetate

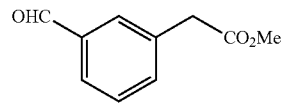

To a solution of 4-methylmorpholine N-oxide (3.58 g, 30.54 mmol) in acetonitrile (22.3 g) was added toluene (19.3 g). Thereto was dropped all of the solution obtained in above Step (ii) at room temperature and the mixture was stirred for 3 hours. After washing with water, the solvent was removed to give the subject compound (1.7 g). Yield: 78%

$^1$H NMR (CDCl$_3$) δ 10.03 (1H, s), 7.83-7.80 (2H, m), 7.59-7.57 (1H, m), 7.54-7.50 (1H, m), 3.73 (2H, s), 3.73 (3H, s).

EXAMPLE 7

6-Amino-2-butoxy-9-{3-[(3-morpholin-4-ylpropyl)amino)]propyl}-7,9-dihidro-8H-purine-8-one dimalonate

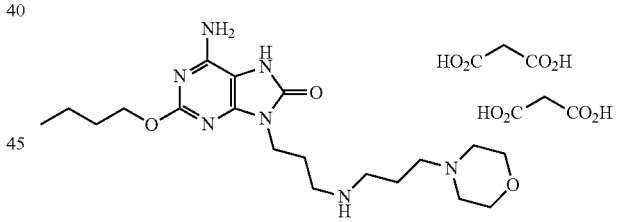

N-(3-Aminopropyl)morpholine (102.54 g, 710.98 mmol) was cooled to 3° C. and thereto was added in a fraction a wetted crystal of 3-(6-amino-2-butoxy-8-methoxy-9H-purine-9-yl)propyl)methanesulfonate (corresponding to dried weight 17.70 g, 47.40 mmol) not to exceed 20° C. After stirring at 28° C. for 10 hours, thereto was added 15% brine (189 g), and the mixture was extracted with a mixture of toluene (230 g) and THF (234 g). After removal of the organic solvent, thereto was added concentrated hydrochloric acid (48 g) and the mixture was stirred at 25° C. Three hours later, the water layer was removed and the organic layer was twice extracted with 10% brine (106 g) and by combining two water layers was obtained an acidic solution. The solution was neutralized with an aqueous 12% sodium hydroxide solution (142 g) and then was made alkaline with 10% sodium carbonate solution (69 g). The solution was extracted with chloroform (528 g) at 50° C. By adding methanol solution (1.40 g) containing malonic acid (9.8 g, 94.80 mmol) at 50° C. to the separated organic layer there was confirmed a crystal. The solution was cooled to 5° C. and the resulting crystal was collected, washed and dried to give the subject compound as a white crystal (21.34 g, 73.1%).

$^1$H NMR (DMSO-d$_6$) δ 9.99 (1H, bs), 8.32 (2H, bs), 6.49 (2H, bs), 4.15 (2H, t, J=8 Hz), 3.76 (2H, t, J=8 Hz), 3.57 (4H, bt, J=5 Hz), 2.94 (8H, s+bt, J=8 Hz), 2.36 (6H, m), 2.00-1.93 (2H, m), 1.75-1.67 (2H, m), 1.67-1.60 (2H, m), 1.43-1.34 (2H, m), 0.92 (3H, t, J=8 Hz).

EXAMPLE 8

Methyl (3-{[[3-(6-amino-2-butoxy-8-oxo-7,8-dihydro-9H-purin-9-yl)propyl](3-morpholin-4-ylpropyl)amino]methyl}phenyl)acetate

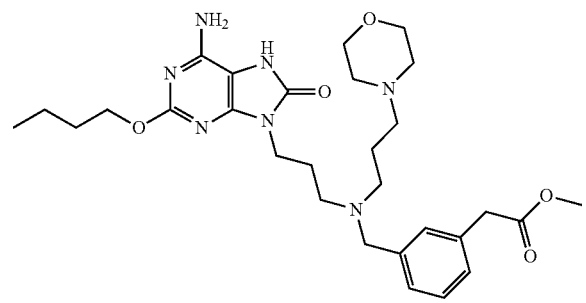 [SMILES: CCCCOc1nc(N)c2[nH]c(=O)n(CCCN(CCCN3CCOCC3)Cc3cccc(CC(=O)OC)c3)c2n1]

To a suspension of 6-amino-2-butoxy-9-{3-(3-morpholin-4-ylpropyl)amino)]propyl}-7,9-dihidro-8H-purine-8-one dimalonate (2.80 g, 4.55 mmol) in NMP (11.5 g) was added at 25° C. triethyamine (1.38 g, 13.64 mmol). After stirring for 10 minutes, thereto was added sodium triacetoxyborohydride (1.64 g, 7.73 mmol), and the mixture was stirred at 25° C. for 10 minutes. After adding methyl (3-formylphenyl)acetate (1.42 g, 7.96 mmol) and stirring at 25° C. for 8 hours, thereto was added NMP (11.5 g) and the mixture was cooled to 5° C., followed by being quenched with cold water 45 g. The solution was adjusted to pH7 with 10% sodium carbonate solution, and thereto was added a seed crystal (10 mg, 0.017 mmol). After stirring for 15 minutes, the solution was adjusted to pH 8 with 10% sodium carbonate solution and thereto was added water. After keeping at 5° C. for 1 hour, the resulting crystal was filtered, washed and dried to give the subject compound (2.48 g, 95.7%).

$^1$H NMR (DMSO-d$_6$) δ 9.82 (1H, bs), 7.24-7.15 (3H, m), 7.10 (1H, d, J=7.3 Hz), 6.39 (2H, bs), 4.11 (2H, t, J=6.6 Hz), 3.67 (2H, t, J=7.2 Hz), 3.64 (2H, s), 3.59 (3H, s), 3.46-3.49 (6H, m), 2.41-2.34 (4H, m), 2.22-2.16 (6H, m), 1.85-1.80 (2H, m), 1.65-1.57 (2H, m), 1.52-1.45 (2H, m), 1.40-1.31 (2H, m), 0.89 (3H, t, J=7.4 Hz).

INDUSTRIAL APPLICABILITY

The present invention relates to a method for preparing an adenine compound useful as a medicament and an intermediate for preparing it.

The invention claimed is:

1. A method for preparing a compound represented by the following formula (1):

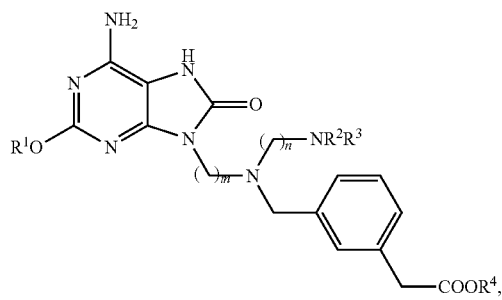

wherein
m and n are independently an integer of 2 to 5,
R$^1$ is chosen from C$_{1-6}$ alkyl groups,
R$^2$ and R$^3$ are the same or different, and are chosen from a hydrogen atom and C$_{1-6}$ alkyl groups, or R$^2$ and R$^3$ are combined with an adjacent nitrogen atom to form pyrrolidine, morpholine, thiomorpholine, piperidine, homopiperidine, piperazine or homopiperazine and the nitrogen atom of position 4 of said piperazine or homopiperazine may be substituted by a group chosen from C$_{1-4}$ alkyl groups, and
R$^4$ is chosen from C$_{1-3}$ alkyl groups, or its pharmaceutically acceptable salt
which is characterized by performing the following steps in the order listed below:

(i) adding a boron-containing reducing agent to
(A) a compound represented by the following formula (2):

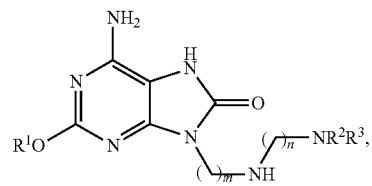

wherein m, n, R$^1$, R$^2$ and R$^3$ are the same as defined above, or (B) a mixture of a salt of the compound represented by the formula (2) and a base; and after at least ten minutes.

(ii) adding a compound represented by the following formula (3):

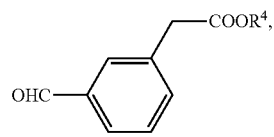

wherein R$^4$ is the same as defined above.

2. The method according to claim 1, wherein the boron-containing reducing agent is sodium triacetoxyborohydride.

3. The method according to claim 1, wherein the method further comprises steps (a) to (c) for preparing a compound represented by formula (2):

Step (a) preparing a compound represented by formula (5):

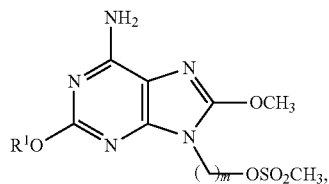

(5)

wherein m and $R^1$ are the same as defined in claim 1,
which comprises reacting a compound represented by formula (4):

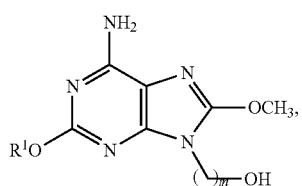

(4)

wherein m and $R^1$ are the same as defined in claim 1, and methanesulfonyl chloride in the presence of a base;

Step (b) preparing a compound represented by formula (7):

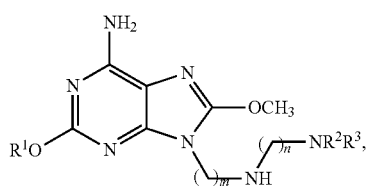

(7)

wherein m, n, $R^1$, $R^2$ and $R^3$ are the same as defined in claim 1, or its salt
which comprises reacting compound (5) prepared by step (a) with a compound represented by formula (6):

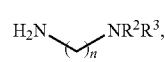

(6)

wherein n, $R^2$ and $R^3$ are the same as defined in claim 1, or its salt;
and then Step (c) preparing (2) or its salt
which comprises treating compound (7) prepared by step (b) with an acid.

4. The method according to claim 3, wherein the acid used in step (c) is chosen from one or more of hydrochloric acid, hydrobromic acid, sulfuric acid, methanesulphonic acid, and toluenesulfonic acid.

5. The method according to claim 4, wherein the acid is 12 to 40% hydrochloric acid.

6. The method according to claim 3, wherein the method further comprises steps (d) to (e) for preparing a compound represented by formula (4):

Step (d) preparing compound of formula (10):

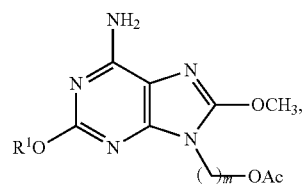

(10)

wherein Ac is acetyl group, and m and $R^1$ are the same as defined in claim 1,
which comprises reacting a compound represented by formula (8):

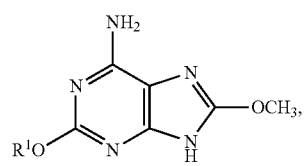

(8)

wherein $R^1$ is the same as defined in claim 1, with a compound represented by formula (9):

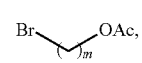

(9)

wherein m and Ac are the same as defined in claim 1, in the presence of a base, and then, Step (e) preparing a compound represented by formula (4):

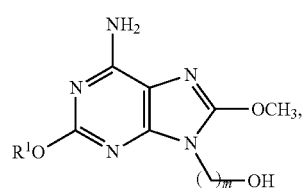

(4)

wherein m and $R^1$ are the same as defined in claim 1,
which comprises hydrolyzing compound (10) prepared in step (d).

7. A compound chosen from compounds represented by following formulae (5), (7) and (10):

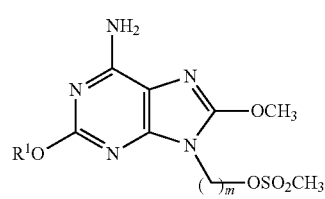

(5)

-continued

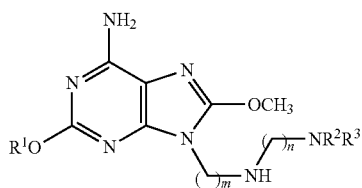
(7)

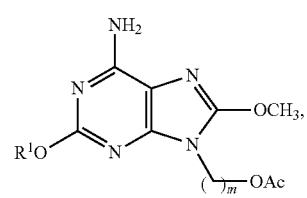
(10)

wherein

Ac is acetyl group, m and n are independently an integer of 2 to 5, $R^1$ is chosen from $C_{1-6}$ alkyl groups, and $R^2$ and $R^3$ are the same or different, and are chosen from a hydrogen atom and $C_{1-6}$ alkyl groups, or $R^2$ and $R^3$ are combined with an adjacent nitrogen atom to form pyrrolidine, morpholine, thiomorpholine, piperidine, homopiperidine, piperazine or homopiperazine and the nitrogen atom of position 4 of said piperazine or homopiperazine may be substituted by a group chosen from $C_{1-4}$ alkyl groups, or a salt thereof.

8. The method according to claim 3, wherein N-methylpyrrolidone, dimethylsulfoxide, or a compound represented by formula (6) serves as a solvent in step (b).

9. The method according to claim 3, wherein 10 to 15 equivalents of compound represented by formula (6) to 1 equivalent of compound represented by formula (5) is used in step (b).

10. The method according to claim 1, wherein m and n are 3, $R^1$ is a butyl group, $R^2$ and $R^3$ are combined with an adjacent nitrogen atom to form morpholine, and $R^4$ is a methyl group.

11. A method for preparing a compound represented by the following formula (2):

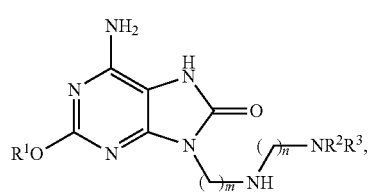
(2)

wherein m and n are independently an integer of 2 to 5, $R^1$ is chosen from $C_{1-6}$ alkyl groups, and $R^2$ and $R^3$ are the same or different, and are chosen from a hydrogen atom and $C_{1-6}$ alkyl groups, or $R^2$ and $R^3$ are combined with an adjacent nitrogen atom to form pyrrolidine, morpholine, thiomorpholine, piperidine, homopiperidine, piperazine or homopiperazine and the nitrogen atom of position 4 of said piperazine or homopiperazine may be substituted by $C_{1-4}$ alkyl group, or its salt, which comprises the following steps:

Step (a) preparing a compound represented by formula (5):

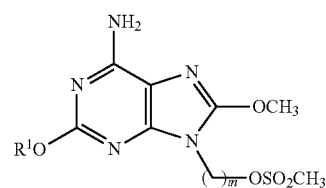
(5)

wherein m and $R^1$ are the same as defined above, which comprises reacting a compound represented by formula (4):

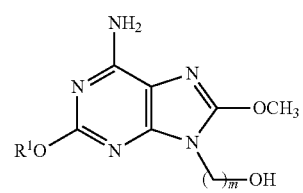
(4)

wherein m and $R^1$ are the same as defined above, and methanesulfonyl chloride in the presence of a base;

Step (b) preparing a compound represented by formula (7):

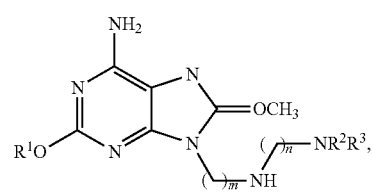
(7)

wherein m, n, $R^1$, $R^2$ and $R^3$ are the same as defined above, or its salt, which comprises reacting the compound represented by formula (5) prepared by Step (a) with a compound represented by formula (6):

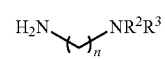

wherein n, $R^2$ and $R^3$ are the same as defined above, or its salt, and

Step (c) preparing a compound represented by formula (2), which comprises treating compound (7) prepared by step (b) with an acid.

12. The method according to claim 11, wherein the acid used in step (c) is chosen from one or more of hydrochloric acid, hydrobromic acid, methansulfonic acid and toluenesulfonic acid.

13. The method according to claim 12, wherein the acid is 12 to 40% hydrochloric acid.

14. The method according to claim 11, wherein m and n are 3, $R^1$ is a butyl group, and $R^2$ and $R^3$ are combined with an adjacent nitrogen atom to form morpholine.

15. A salt of 6-amino-2-butoxy-9-(3-[(3-morpholin-4-yl-propyl)amino)propyl}-7,9-dihydro-8H-purine-8-one chosen from maleates, fumarates, malonates, and oxalates of 6-amino-2-butoxy-9-(3-[(3-morpholin-4-ylpropyl)amino)propyl}-7,9-dihydro-8H-purine-8-one.

16. The compound according to claim 15, which is 6-amino-2-butoxy-9-{3-[(3-morpholin-4-ylpropyl)amino]propyl)-7,9-dihydro-8H-purine-8-one dimaleate.

17. The compound according to claim 15, which is 6-amino-2-butoxy-9-{3-[(3-morpholin-4-ylpropyl)amino]propyl)-7,9-dihydro-8H-purine-8-one dimalonate.

18. 6-amino-2-butoxy-9-(3-[(3-morpholin-4-ylpropyl)amino)propyl}-7,9-dihydro-8H-purine-8-one trihydrochloride.

\* \* \* \* \*